(12) United States Patent
Jacobson et al.

(10) Patent No.: US 6,815,218 B1
(45) Date of Patent: Nov. 9, 2004

(54) METHODS FOR MANUFACTURING BIOELECTRONIC DEVICES

(75) Inventors: Joseph M. Jacobson, Newton, MA (US); Scott Manalis, Cambridge, MA (US); Brent Ridley, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/590,044

(22) Filed: Jun. 8, 2000

Related U.S. Application Data
(60) Provisional application No. 60/138,332, filed on Jun. 9, 1999.

(51) Int. Cl.$^7$ ................................................ H01L 21/00
(52) U.S. Cl. .............................. 438/1; 438/49; 438/800
(58) Field of Search .............................. 438/1, 49, 800, 438/8; 257/40, 252, 253, 414

(56) References Cited

U.S. PATENT DOCUMENTS

| | | | | |
|---|---|---|---|---|
| 3,865,550 A | * | 2/1975 | Bott et al. ................. | 23/232 E |
| 5,605,662 A | * | 2/1997 | Heller et al. ................ | 422/68.1 |
| 5,837,832 A | | 11/1998 | Chee et al. ................. | 536/22.1 |
| 5,874,219 A | | 2/1999 | Rava et al. ..................... | 435/6 |
| 6,207,392 B1 | * | 3/2001 | Weiss et al. .................. | 435/7.1 |
| 6,303,943 B1 | * | 10/2001 | Yu et al. ......................... | 257/40 |
| 6,399,303 B1 | * | 6/2002 | Connolly ........................ | 435/6 |

OTHER PUBLICATIONS

Keller et al., "A Chemical Method for Introducing Haptens onto DNA Probes," *Analytical Biochemistry*, vol. 170, 1988, pp. 441–450.

Steigerwald et al., "Surface Derivatization and Isolation of Semiconductor Cluster Molecules," *Journal of the American Chemical Society*, vol. 110, No. 10, May 11, 1988, pp. 3046–3050.

Jarvis et al., "Solution Synthesis and Photoluminescence Studies of Small Crystallites of Cadmium Telluride," *Materials Research Society Symposium Proceedings*, vol. 272, Apr. 1992, pp. 229–234.

Murray et al., "Synthesis and Characterization of Nearly Monodisperse CdE (E=S, Se, Te) Semiconductor Nanocrystallities," *Journal of the American Chemical Society*, vol. 115, 1993, pp. 8706–8715.

Dabbouoi et al., "Langmuir–Blodgett Manipulation of Size–Selected CdSe Nanocrystallities," *Chemistry of Materials*, vol. 6, No. 2, Feb. 1994, pp. 216–219.

Health et al., "Pressure/Temperature Phase Diagrams and Superlattices of Organically Functionalized Metal Nanocrystal Monolayers: The Influence of Particle Size, Size Distribution, and Surface Passivant," *Journal of Physical Chemistry B*, vol. 101, No. 2, Jan. 9, 1997, pp. 189–197.

Alivisatos, "Electrical Studies of Semiconductor–Nanocrystal Colloids," *MRS Bulletin*, vol. 23, No. 2, ISSN: 0883–7694, Feb. 1998, pp. 18–23.

Souteyrand et al. "Direct Detection of the Hybridization of Synthetic Home Oligomer DNA Sequences by Field Effect," *J. Phys. Chem. B*, vol. 101, (1997) pp. 2980–2985.

* cited by examiner

*Primary Examiner*—W. David Coleman
(74) *Attorney, Agent, or Firm*—Testa, Hurwitz & Thibeault LLP

(57) ABSTRACT

Bioelectronic components are formed using nanoparticles surrounded by attached shells of at least one biological material. The nanoparticles are deposited (e.g., using a printing process) onto a surface, and by associating the deposited nanoparticles with one or more electrical contacts, electrical measurement across the nanoparticles (and, consequently, across the biological material) may be made. A finished component may include multiple layers formed by nanoparticle deposition.

13 Claims, 4 Drawing Sheets

METHODS FOR MANUFACTURING BIOELECTRONIC DEVICES

RELATED APPLICATION

This application stems from U.S. Provisional Application Ser. No. 60/138,332, filed on Jun. 9, 1999.

BACKGROUND OF THE INVENTION

1. Field of the Invention

The present invention relates to fabrication of electronic structures involving biological or biochemically components.

2. Background Information

Electronic and electromechanical components are presently fabricated in large, industrial manufacturing facilities that are tremendously expensive to build and operate. For example, semiconductor device fabrication generally requires specialized microlithography and chemical etching equipment, as well as extensive measures to avoid process contamination.

The fabrication processes ordinarily employed to create electronic and electromechanical components are expensive and limited in the quantities, which they can produce. In addition they typically involve harsh conditions such as high temperatures and/or caustic chemicals. The ability to integrate the manufacture of such electronic and electromechanical components with biological and biorganic molecules is becoming increasingly important. An example of this integration is the so-called "biochip," i.e., an electronically active or readable substrate having a dense array of different biological materials (e.g., DNA probes). Such a chip can be used, for example, to identify samples of interest or to test for the presence of various molecular sequences. See, e.g., U.S. Pat. Nos. 5,605,662, 5,874,219, and 5,837,832.

SUMMARY OF THE INVENTION

The present invention provides an alternative to traditional fabrication of electronic components that is economical, scalable and facilitates incorporation of delicate materials. In particular, the invention utilizes nanoparticles to create, through deposition and pattering, microelectronic devices that incorporate biological materials. As used herein, the term "biological material" means any biological, biorganic, or organic material exhibiting biological activity or capable of interacting with a biologically active material; examples of biological materials include, without limitation, proteins, polypeptides (ranging from small oligopeptides to large functional molecules), nucleic acids, polysaccharides, carbohydrates, enzyme substrates, antigens, antibodies, pharmaceuticals, etc.

In accordance with the invention, one or more biological materials are associated, either by direct chemical bonding or by contact, with electrically active materials provided (at least initially) in the form of nanoparticles. In one aspect the invention exploits the fact that many physical, electrical, and optical properties that appear constant in the bulk of organic and inorganic materials are size-dependent at the very small scales characteristic of nanoparticles. At these sizes—ranging from nearly 1 to 999 nm—the ratio of surface atoms to interior atoms becomes non-negligible, and particle properties therefore lie between those of the bulk and atomic materials. Monodisperse (i.e., uniformly sized) or polydisperse nanoparticles can form stable colloids in appropriate dispersing media, facilitating their deposition and processing in a liquid state. As a result printing technology can be utilized to deposit and pattern nanoparticles.

Furthermore, a key property that changes at small sizes is melting point. The effect is substantial; in some semiconductors, melting points have been observed to drop more than 1000° C. from the bulk material. The melting point depression observed in nanoparticle systems facilitates the low-temperature sintering, annealing, and melting of nanoparticles into crystalline films. As a result, nanoparticles can be printed and heated at low temperatures to form films of the bulk material, in some cases without damage to associated biological materials, or can instead be printed and left in dispersed form to retain the size-dependent properties characteristic of the nanoparticles. Alternatively nanoparticles may be printed to form electronic, microelectromechanical or microfluidic devices and then subsequently biological material may be printed or added to form a bioelectronic component.

Unlike conventional electrically active particles, nanoparticles are formed not by grinding, but instead via chemical methods (such as pyrolysis) or physical methods (such as physical vapor synthesis). Nanoparticles useful in accordance with the present invention may be pristine or surrounded by a "capping" group to passivate the surface, alter surface chemistry, facilitate dispersion in a liquid, or, in many applications, to bind a biological material. Following their deposition, nanoparticles can self-assemble to form highly ordered thin films and superlattices that may exhibit multiple phases.

Accordingly, in a preferred embodiment, the invention comprises a method of fabricating a bioelectronic component. In accordance with the method, nanoparticles are surrounded by attached shells of at least one biological material. The nanoparticles may then be deposited (e.g., using a printing process) onto a surface. By associating the deposited nanoparticles with one or more electrical contacts, electrical measurement across the nanoparticles (and, consequently, across the biological material) may be made. The device may include a plurality of layers formed by nanoparticle deposition. The nanoparticles within each deposited layer may be immobilized (by fusing, melting, or annealing the particles into a continuous material, by curing the carrier into a permanent matrix, by surrounding the nanoparticles with bifunctional surface groups that link adjacent nanoparticles, or merely by evaporating the carrier using heat or low pressure) in order to facilitate performance of the intended function. Also within the scope of the invention are components fabricated in accordance with the methods hereof.

BRIEF DESCRIPTION OF THE DRAWINGS

The invention description below refers to the accompanying drawings, of which.

DETAILED DESCRIPTION OF AN ILLUSTRATIVE EMBODIMENT

1. Nanoparticle Synthesis and Suspension

Figure 1:
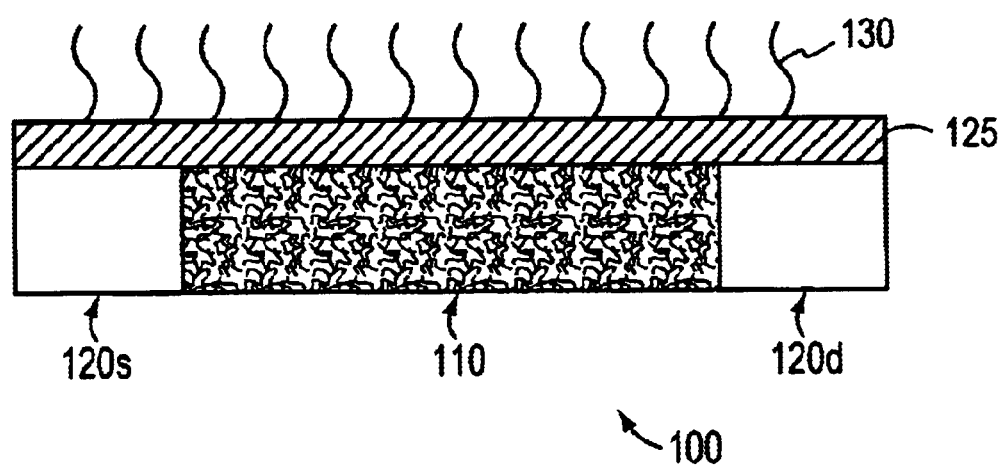
FIG. 1 is a greatly enlarged side elevation of a chemFET transistor device fabricated in accordance with the present invention.

Particles useful in accordance with the present invention may be monodisperse or polydisperse, and may represent a homogeneous suspension of a single species of nanoparticle or a heterogeneous suspension of different nanoparticles. Representative classes of nanoparticle include insulators (e.g., silicon dioxide); semiconductors (e.g., silicon or cadmium selenide); and conductors (e.g., gold or silver).

Numerous synthetic approaches, including pyrolysis of organometallic precursors, arrested precipitation, precipitation in reverse micelles, and exchange (metathesis) reactions, have been used to generate nanoparticles. See, e.g., Alivisatos, "Electrical Studies of Semiconductor-Nanocrystal Colloids," *MRS Bulletin*, Feb. 1998, at 18–23. In principle, virtually any nanoparticle synthesis is appropriate for the production of nanoparticles for the purposes of the present invention. However, because nanoparticle properties depend strongly on size, shape, crystallinity, and surface derivatization, in practice the particle synthesis is tailored so as to control these parameters for a particular application. In general, if the nanoparticles are not intended for bulk thick or thin film deposition—i.e., they will be applied and utilized in their native particulate state without subsequent fusion into the bulk material—then any synthesis yielding appropriate size control and crystallinity can be utilized.

On the other hand, if the particles are printed as a precursor to bulk thick or thin films, the synthesis should yield particles without tightly bound or heavy capping groups. Capping groups (sometimes used during synthesis to retard particle growth) can be problematic in bulk film applications if they become trapped as impurities or impede crystal growth, thereby compromising film quality. Pyrolytic syntheses using pyridines and other coordinating solvents (see, e.g;, Murray et al., *J. Am. Chem. Soc.* 115:8706 (1993)), micelle-based approaches (see, e.g., Steigerwald et al., *J. Am. Chem. Soc.* 110:3046 (1988)), and some metathetic preparations (see, e.g., Jarvis et al., *Mat. Res. Soc. Symp. Proc.* 272:229 (1992)) can all yield particles free of heavy organic capping groups. U.S. application Ser. No. 09/334,873, filed on Jun. 17,1999 and hereby incorporated by reference, discloses techniques of metathesis synthesis to form very small particles without the use of heavy capping groups.

Although in some circumstances it is possible to attach biological materials directly to a nanoparticle, attachment is more generally facilitated by surrounding the nanoparticles with an organic capping group, which envelopes the typically inorganic particle core as a shell capable of binding to biological molecules of interest. For example, silicon nanoparticles can be coated with 3-aminopropyltriethoxysilane (present, for example, as a 5% aqueous solution in which the nanoparticles are dispersed). Single-stranded DNA may then be coupled to the coated nanoparticles using the well-known N-bromosuccinimide method (see Keller et al., *Anal. Biochem.* 170:441 (1988)). As an alternative example, proteins may be conveniently linked to gold nanoparticles by a chemical linkage of said gold nanoparticle to a cysteine amino acid group either naturally present in the protein or engineered to be present in the protein.

Additionally, the capping groups can act as a critical component in a device. For example, the caps (including attached biomolecules) can act as electrical insulators or sensitizers.

Nanoparticles are known to self-assemble into ordered arrays and superlattices, both with and without capping groups. If such ordered films orient not only particles but also their crystal planes, then long-range crystal order may be expected upon sintering, annealing, or melting. Highly faceted particles may be more likely to align their crystal planes than unfaceted particles. Self-assembly also offers the possibility of printing multiple phases or layers in a single pass, or for printing some pre-assembled structures or structures that assemble during the printing. Thus, different layers or regions might form as a result of a single printing step. Layers may form by size affinity, with large and small particles tending to group with other particles of similar size. See, e.g., Heath et al., *J. Phys. Chem.* B 101:189 (1997) and Dabbousi et al., *Chem. of Mat'ls.* 6:216 (1994), showing size-based particle clustering. Three-dimensional structures have been observed to occur when particles of different sizes are brought together and small particles cluster around single large ones.

2. Applications

Nanoparticles suspended in a liquid can be deposited and patterned onto a substrate using any of a wide variety of processes, including ink jetting, spincoating, casting, lithography, gravure printing, screen printing, impact printing, stamping, embossing, contact printing (whereby a liquid or solid pattern is transferred from a plate, stamp or cylinder), or transfer onto the substrate through a mask. Moreover, nanoparticles may be applied in the dry state by dry jetting, laser printing or electrophotography (whereby a substrate receives a charge pattern and the particles are drawn to the charged regions). Deposition or application may generally occur in an uncontrolled atmospheric environment, but a controlled atmosphere generally provides better process control. The deposited layers may serve as conductive, semiconductive, or insulating layers, chemically or biologically active layers, or as etch resists, light barriers, diffusion barriers, passivation layers, adhesion layers, encapsulants, or structural supports.

A representative application of the present invention is fabrication of chem-FETs. In a traditional field-effect transistor, the electrical resistance of the current path between source and drain elements is varied by applying a voltage to the gate element, which is separated from source and drain by a dielectric. In a chemFET, the metal gate element is removed, and the dielectric used as a sensor surface. When charged species such as polar molecules or ions bind to the dielectric, the source-drain conductivity is altered, and this change can be detected and measured through operation of the device. Accordingly, by appropriately tailoring the transistor structure, specific chemicals or reactions may be sensed through their interaction with the transistor surface. For example, if biological material comprises single-stranded oligonucleotides, hybridization of the oligonucleotides may be detected (see Souteyrand et al., *J. Phys. Chem.* B 101:2980 (1997)). Attachment of the biological material may be by specific chemical interaction with the surface of the nanoparticle or nanoparticle-derived film. As another example an antibody may be attached to the surface of the printed chemfet enabling electronic detection of antigen binding.

As shown in FIG. 1, a chemFET 100 in accordance with the present invention comprises a semiconductor layer 110, source and drain elements 120d, 120s, and a dielectric layer 125 applied thereover. Semiconductor layer 110 may be formed by deposition of nanoparticulate CdSe, CdS, CdTe, Si, or other semiconductor onto a suitable substrate (not shown). Source and drain elements 120*d*, 120*s* may be formed from nanoparticle silver, chromium, gold, copper, aluminum or other metallic dispersion. To form layer 125, a nanoparticle dispersion of silicon dioxide or barium titanate is deposited onto the coplanar surfaces of semiconductor layer 110 and source and drain elements 120*d*, 120*s*. These materials may be left as deposited, or may instead be sintered, annealed, or melted to form layers with electronic properties approaching those of the bulk material. Annealing, for example, can take place during printing, after each printing step, or following deposition. As with any bulk film, annealing can consist of multiple stages of treatment at different temperatures (e.g., temperature rampup and/or thermal shock), heating mechanisms, durations, or ambients to improve selected electrical and/or mechanical properties. To anneal the particles, the temperature of the environment is elevated to a point high enough to remove the capping groups (if any) and to cause fusion, annealing, or melting of particles in all layers for which a bulk film is desired. Alternatively, electromagnetic radiation, such as from a heat lamp or laser, may be used to thermally convert the nanoparticles to their bulk state.

This configuration facilitates the detection of specific biological materials 130 disposed on layer 125. In the case of oligonucleotides, for example, hybridization with complementary nucleic-acid strands can be detected. Layer 125 may be configured for interaction with biological material 130 in any of various ways. In one approach, layer 125 is an insulator film fabricated by sintering a deposited nanoparticle colloid and subsequently treating the material to expose reactive hydroxyl groups that bind with the biological material. In one instance such biological material may be disposed on the insulator by means of printing or micospotting the biological material onto the appropriate location. Alternatively they may be self assembled by means of specific chemical interactions with layer 125 or electrostatically assembled by applying a potential to the device electrodes. In certain cases dielectric layer 125 may be obviated and biological material 130 attached directly to semiconducting layer 110.

The transistor illustrated in FIG. 1 may be connected to other printed or non-printed components to form functional electronic circuits. The means of connection may, for example, be established by deposition of nanoparticle conductors and, if necessary, insulators. These circuits may be connected to other printed or non-printed electronic, mechanical, chemical, or electromechanical devices.

Figure 2:
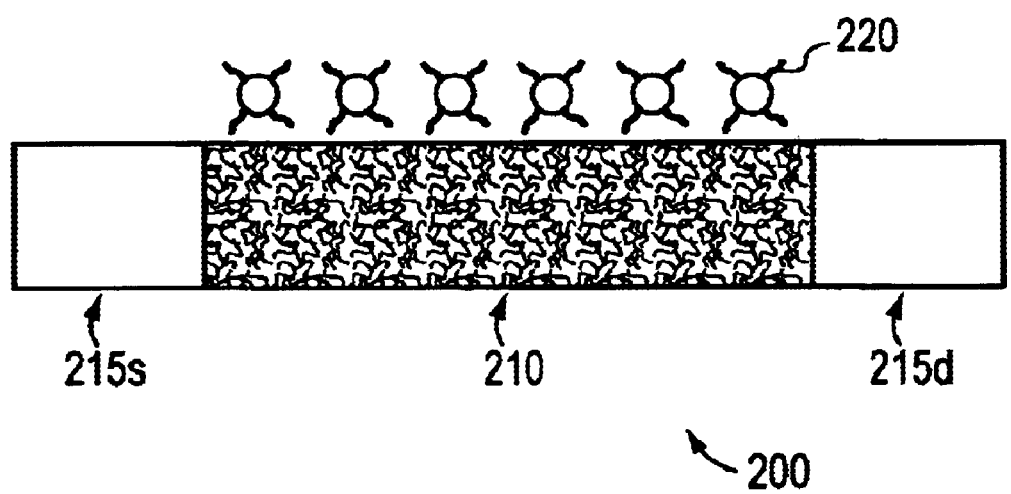
FIG. 2 is a greatly enlarged side elevation of an alternative chemFET transistor.

Alternatively, a dielectric layer can consist of unsintered nanoparticles. These may either be insulating nanoparticles or beads with attached biological material. Alternatively they may be conducting or semiconducting and will collectively act as an insulator due to retention of the capping group, which thereby provides sites for chemical modification (so that the biological material reacts with the cap, or a material subsequently bound to the cap, rather than with the inorganic nanoparticle material). Referring to FIG. 2, a chemFET 200 comprises a semiconductor layer 210, a source element 215*s*, and a drain element 215*d*. These constituents may be fabricated as discussed above, i.e., by deposition and sintering of nanoparticles having appropriate conductivities. A layer 220 of nanoparticles having a biological material of interest attached thereto is applied onto semiconductor layer 210 between source and drain elements 215*d*, 215*s*. Such nanoparticles with attached biological material would generally be insulating nanoparticles or beads with directly bound biological material. Alternatively they could be conducting or semiconducting nanoparticles with appropriate capping groups. Such biological material may be positioned appropriately in one instance by means of printing or microspotting the biological material. Alternatively said biological material be self assembled by means of specific chemical interaction or electrostatically assembled by applying a potential to the device electrodes.

In one exemplary embodiment, monoclonal antibodies are attached to nanoparticles 220 in the manner presently used to attach them to latex beads and other stationary supports. The various fractions of an electrophoretic protein separation are passed over the layer 220, and when a binding fraction is reached, the binding reaction is revealed by the change in measured electrical current from source to drain. In another embodiment, nucleic-acid probes are attached to nanoparticles 220, and candidate nucleic-acid fragments are passed over the layer 220. When a complementary fragment hybridizes with the bound probes, this is once again revealed by the change in measured electrical current from source to drain.

Referring to the preceding description of device 200, an alternative configuration is one in which layer 220 is obviated and biological material is instead bound directly to conducting or semiconducting nanoparticles which are then further disposed, unsintered, between electrodes 215*d* and 215*s*. The same types of biological materials, the same ways to dispose them in the appropriate location and similar electrical readout means obtain.

Figure 3:
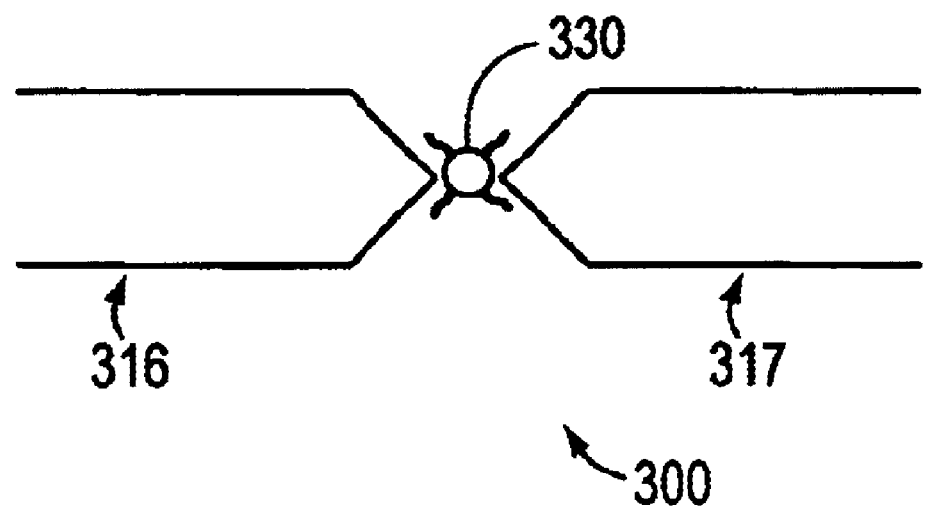
FIG. 3 is a greatly enlarged depiction of a SET transistor device fabricated in accordance with the present invention.

FIG. 3 illustrates formation of a single-electron transistor (SET). Like chemFETs, SETS can detect the absorption of charged material. The advantages of SETs are, first that the gate is on the length scale of single molecules, and second, that the charge sensitivity is several orders of magnitude greater. In accordance with this approach, illustrated in FIG. 3, a SET 300 is self-assembled by binding a single nanoparticle 330 between two conducting contacts 315, 317. The contacts may, for example, be synthesized carbon nanotubes with modified chemical ends such that the nanoparticle self assembles onto them. Alternatively electrodes may be formed by printing conductive nanoparticles or by conventional photolithographic or other means and then employing electromigration, electroplating or electrofusing under feedback control to realize the nanoscale electrode spacing required for single electron transistor operation. Thus formed, contacts 315, 317 are exposed to a solution of nanoparticles having capping groups and, radiating therefrom (typically as a tangle of minute threads), biomolecules of interest. The interelectrode spacing distance approximates the size of the nanoparticles, so that a single nanoparticle can lodge between the electrodes and bridge them. Reagents affecting the biological material may be directly adsorbed onto (or absorbed into) the nanoparticle, and the effect monitored by operation of the device.

As described, a SET typically consists of a single nanoparticle disposed between two nanoelectrodes and insulated from those nanoelectrodes by means of insulating capping groups. An alternative arrangement consists of a chain of nanoparticles between electrodes insulated from each other and from the electrodes by means of insulating capping groups. Such a chain may be formed by applying an electric field to the electrodes in the presence of a solution of nanoparticles. Conduction is by means of electron hopping. If the nanoparticles have associated with them biological material, then the hopping probability and thus the current flow is affected by other molecules interacting with the associated biological material and may be measured.

In addition to chemFETs and SETs, electrometers for sensing charged material can also be fabricated using a technology known as light-addressable potentiometer systems (LAPs) or single point potential (SPP) electrometers. The principle is nearly identical to that underlying chemFETs except that only one electrode per device is required. These devices, too, can be printed with nanoparticle technology.

For biochips, many reactions are analyzed in parallel, requiring arrays of integrated sensors. Devices such as chemFETs, SETs, or SPPs can be printed in arrays where rows and columns are isolated from each other (as described, for example, in copending application Ser. No. 08/820,057, filed on Mar. 18, 1997 and entitled PRINTABLE ELECTRONIC DISPLAY). A memory circuit can also be constructed using printed SETs in accordance with copending application Ser. No. 09/291,801, filed on Apr. 14, 1999 and entitled MEMORY STRUCTURES AND METHODS OF MAKING SAME. The entire disclosures of both of these applications are hereby incorporated by reference.

In another application of SET technology, a polymerase molecule (generally bound to a nanoparticle) is suspended between SET electrodes. Nucleic-acid polymerases are enzymes that catalyze synthesis of a nucleic-acid chain based on a template. In the presence of appropriate nucleosides, a polymerase follows the template (which may be single or double-stranded DNA, or RNA) and causes synthesis of its complement. In accordance with one aspect of the present invention, the applied field is used to sense the conformational change of the enzyme during synthesis, thereby revealing the sequence of the template strand (as well as the synthesized strand). That is, the electrical signal produced by the SET during the course of synthesis encodes the identity of the template and synthesized strands, since the conformational changes—and the corresponding effects on current flow through the SET—of the polymerase are characteristic for particular bases.

In a related aspect, the synthetic action of the polymerase is directed rather than merely observed. The polymerase enzyme functions by means of a catalytic reaction crevice whose conformational attributes are altered slightly by interaction with a nucleotide base from the template. Using one or more nanoelectrode or STM tips applied to the polymerase, the molecule can be caused to selectively assume conformational changes, which will induce 'errors' in the copy of a homopolymer template. Such 'errors' may encode data either as memory or to be fed into another polymerase attached to a SET readout. Such a system thus realizes the basic components of a read and write memory system.

Figure 4:
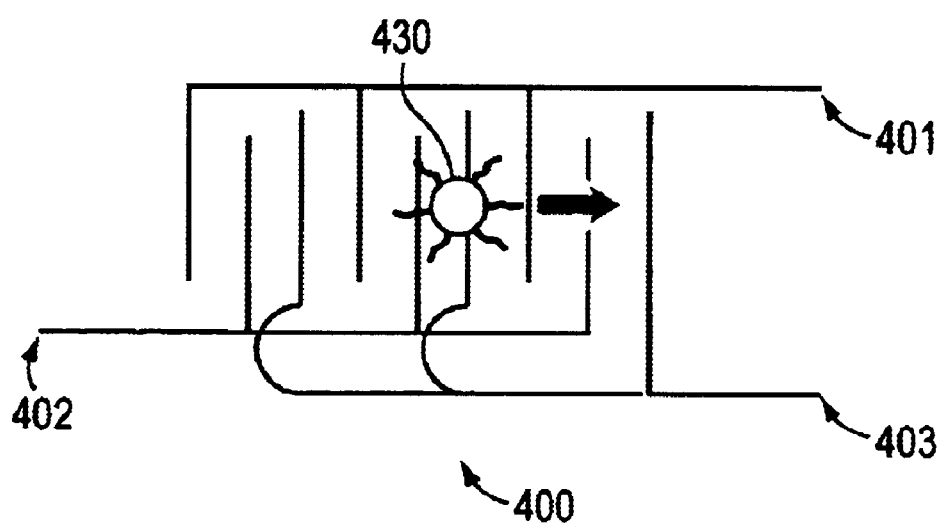
FIG. 4 is a greatly enlarged microfluidics device fabricated in accordance with the present invention.

FIG. 4 illustrates an electrically controllable microfluidic. In this case, a linear drive motor 400, which is useful for transporting biological molecules which may be bound to nanoparticles or beads 430 for the purpose of carrying out chemistry and transport. The device is created by printing conducting nanoparticles to form the three phases 401, 402 and 403 of three phase linear drive motor. In addition walls or fluidic channels may be printed for containment of a fluid media.

Although the present invention has been described with reference to specific details, it is not intended that such details should be regarded as limitations upon the scope of the invention, except as and to the extent that they are included in the accompanying claims.

What is claimed is:

1. A method of fabricating a bioelectronic component, the method comprising the steps of:
   a. providing a batch of nanoparticles having submicron sizes and an electrical characteristic;
   b. attaching at least one biological material to the nanoparticles so as to form shells of the biological material therearound, wherein the biological material is selected from the group consisting of proteins, polypeptides, nucleic acids, polysaccharides, carbohydrates, enzyme substrates, antigens, antibodies, pharmaceuticals, and combinations thereof;
   c. depositing onto a surface the nanoparticles coated with shells attached thereto; and
   d. causing the deposited nanoparticles to be in electrical communication with at least one electrical contact to facilitate an electrical measurement thereof, the electrical measurement being affected by the biological material.

2. The method of claim 1 in which the nanoparticles are caused to be in electrical communication with said electrical contact by self-assembly.

3. The method of claim 1 in which the nanoparticles are caused to be in electrical communication with said electrical contact by electrostatic assembly.

4. The method of claim 1 wherein the nanoparticles are semiconductive.

5. The method of claim 1 wherein the nanoparticles are conductive.

6. The method of claim 1 wherein the nanoparticles, surrounded by the biological material, collectively act as an insulator.

7. The method of claim 1 wherein the component is a transistor comprising a source element and a drain element and a semiconductor layer disposed between the source and the drain elements, and depositing the nanoparticles onto a surface comprises depositing the nanoparticles onto the surface of the semiconductor layer.

8. The method of claim 1 repeated at a plurality of locations on a substrate to form an array of bioelectronic components.

9. A method for fabricating a biolectronic component, the method comprising the steps of:
   a. providing a first batch of nanoparticles having submicron sizes and a first electrical characteristic;
   b. depositing the first batch of nanoparticles onto a surface;
   c. sintering the first batch of nanoparticles to form a continuous, uniform layer exhibiting the electrical characteristic of the first batch of nanoparticles, the layer having a surface;
   d. providing a second batch of nanoparticles having submicron sizes and a second electrical characteristic;
   e. attaching at least one biological material to the second batch of nanoparticles so as to form shells of the shells of the biological material therearound;
   f. depositing the second batch of nanoparticles onto the layer surface formed by the first batch of nanoparticles;
   g. causing the deposited second batch of nanoparticles to be in electrical communication with at least one electrical contact to facilitate an electrical measurement thereof, the electrical measurement being affected by the biological material.

10. A method for fabricating a bioelectronic component, the method comprising the steps of:
   a. providing a first batch of nanoparticles having submicron sizes and a first electrical characteristic;
   b. depositing the first batch of nanoparticles onto a surface;
   c. sintering the first batch of nanoparticles to form a continuous, uniform layer exhibiting the electrical characteristic of the first batch of nanoparticles, the layer having a surface;

d. providing a second batch of electrically conductive nanoparticles having submicron sizes;

e. depositing the second-batch nanoparticles in contact with a portion of the layer derived from the first batch of nanoparticles; and f. sintering the second-batch of nanoparticles to form an electrical contact, g. providing a third batch of nanoparticles having submicron sizes and a second electrical characteristic;

h. attaching at least one biological material to the third batch of nanoparticles so as to form shells of the shells of the biological material therearound;

i. depositing the third batch of nanoparticles onto the layer surface formed by the first batch of nanoparticles;

j. causing the deposited second batch of nanoparticles to be in electrical communication with the electrical contact to facilitate an electrical measurement thereof, the electrical measurement being affected by the biological material.

11. The method of claim 10 further comprising the steps of repeating steps (a)–(j) at a plurality of locations on a substrate to form an array of bioelectronic components.

12. The method of claim 1 wherein the biological material comprises at least one nucleic acid.

13. The method of claim 1 wherein the biological material comprises at least one protein.

* * * * *